(12) United States Patent
Leverrier et al.

(10) Patent No.: US 7,798,005 B2
(45) Date of Patent: Sep. 21, 2010

(54) RESONATOR MEASUREMENT DEVICE AND METHOD EMPLOYING THE DEVICE

(75) Inventors: Bertrand Leverrier, Montelier (FR); Olivier Lefort, Valence (FR)

(73) Assignee: Thales (FR)

( * ) Notice: Subject to any disclaimer, the term of this patent is extended or adjusted under 35 U.S.C. 154(b) by 306 days.

(21) Appl. No.: 11/722,954

(22) PCT Filed: Dec. 20, 2005

(86) PCT No.: PCT/EP2005/056961

§ 371 (c)(1),
(2), (4) Date: Mar. 18, 2008

(87) PCT Pub. No.: WO2006/069937

PCT Pub. Date: Jul. 6, 2006

(65) Prior Publication Data

US 2008/0184804 A1    Aug. 7, 2008

(30) Foreign Application Priority Data

Dec. 27, 2004  (FR)  ................................. 04 13965
Jan. 20, 2005  (FR)  ................................. 05 00591

(51) Int. Cl.
*G01L 11/00* (2006.01)

(52) U.S. Cl. .......................................... 73/702; 73/708

(58) Field of Classification Search ........................ None
See application file for complete search history.

(56) References Cited

U.S. PATENT DOCUMENTS

| 5,009,108 | A | | 4/1991 | Harada et al. |
| 5,165,289 | A | | 11/1992 | Tilmans |
| 5,458,000 | A | * | 10/1995 | Burns et al. ................ 73/708 |
| 5,546,810 | A | | 8/1996 | Arikawa et al. |
| 6,085,594 | A | | 7/2000 | Gutierrez et al. |
| 6,119,523 | A | * | 9/2000 | Olsson et al. ................. 73/718 |
| 6,367,786 | B1 | * | 4/2002 | Gutierrez et al. ............ 267/136 |
| 6,584,845 | B1 | * | 7/2003 | Gutierrez et al. ......... 73/514.15 |
| 7,334,481 | B2 | * | 2/2008 | Correale ....................... 73/702 |

(Continued)

FOREIGN PATENT DOCUMENTS

FR    2 687 783    8/1993

(Continued)

OTHER PUBLICATIONS

Byeungleul, Lee et al., "A Study on Wafer Level Vacuum Packaging for MEMS Devices", Journal of Micromechanics & Microengineering, Institute of Physics Publishing, Bristol, GB, vol. 13, No. 5, Sep. 2003, pp. 663-669, XP002359219, ISSN: 0960-1317.

(Continued)

*Primary Examiner*—Lisa M Caputo
*Assistant Examiner*—Jermaine Jenkins
(74) *Attorney, Agent, or Firm*—Lowe Hauptman Ham & Berner, LLP

(57) ABSTRACT

The invention relates to a device and a method for detecting a fault in a measurement device comprising a resonator and means for measuring a resonant frequency of the resonator. According to the invention, the device further includes means delivering information ($S_3$) representative of the quality factor of the resonator (3) at the resonant frequency.

16 Claims, 2 Drawing Sheets

U.S. PATENT DOCUMENTS 7,444,878 B1 * 11/2008 Pepples ..................... 73/722

FOREIGN PATENT DOCUMENTS

FR        2 834 055        6/2003
FR        2 848 298        6/2004

OTHER PUBLICATIONS

Parsons, P., et al., "Resonant Sensors for High Accuracy Pressure Measurement Using Silicon Technology", Proceedings of the National Aerospace and Electronics Conference (NAECON), Dayton, May 18-22, 1992, New York, IEEE, US, vol. 1, Conf. 44, May 18, 1992, pp. 349-355, XP00 339598, ISBN: 0-7803-0652-X.

* cited by examiner

RESONATOR MEASUREMENT DEVICE AND METHOD EMPLOYING THE DEVICE

CROSS-REFERENCE TO RELATED APPLICATIONS

The present Application is based on International Application No. PCT/EP2005/056961 filed on Dec. 20, 2005, which in turn corresponds to France Application No. 04 13965 filed on Dec. 27, 2004 and France Application No. 05 00591, filed on Jan. 20, 2005, and priority is hereby claimed under 35 USC §119 based on these applications. Each of these applications are hereby incorporated by reference in their entirety into the present application.

FIELD OF THE INVENTION

The present invention relates to the field of aeronautics, and more particularly, to a device and a method for detecting a fault in a measurement device comprising a resonator and means for measuring a resonant frequency of the resonator.

BACKGROUND OF THE INVENTION

The invention relates to a device and a method for detecting a fault in a measurement device comprising a resonator and means for measuring a resonant frequency of the resonator. The measurement device comprises, for example, a fluid pressure sensor. The invention is particularly useful in aeronautics, in which pressure measurements are of paramount importance for controlling the flight of an aircraft. This is because the altitude of a flight level required for an aircraft is determined by the static pressure of the air surrounding the aircraft. Moreover, since air traffic is increasing, traffic control authorities seek to reduce the difference between two neighboring flight levels. It is essential to detect a defect in a pressure sensor in order to guarantee air traffic safety.

The invention may also be employed for other devices using a resonator, such as for example in an accelerometer, as described in French Patent Application FR 2 848 298, a gyro, as described in French Patent Application FR 2 834 055, or else in a timebase. The rest of the description will be given solely with reference to an air pressure sensor, without of course limiting the invention.

To measure the pressure of the ambient air, it is common practice to use pressure sensors comprising a chamber maintained at a reference pressure, generally close to vacuum. An example of this type of sensor is described in French Patent Application FR 2 687 783. The pressure sensor measures a pressure difference between the chamber and the air. The guarantee of the precision in the pressure measurement essentially depends on maintaining the vacuum within the chamber over the lifetime of a sensor, or at the very least between two calibrations of the pressure sensor. Several effects may degrade the vacuum within the chamber, such as in particular leaks that may occur at the joints of various components of the walls of the chamber or else outgassing from the walls or from the components located in the chamber.

The pressure sensor described in French Patent Application FR 2 687 783 includes a resonator, one end of which is exposed to a force that depends on the pressure difference between the inside of the chamber and the ambient air. The principle of the pressure measurement consists in measuring the resonant frequency of the resonator.

Moreover, it has been shown that, at constant air pressure, the ambient temperature has an influence on the resonant frequency. It is possible to add a temperature sensor to the pressure sensor. During a calibration phase, a function combining the measured temperature and the resonant frequency is established in order to determine the pressure. This function may be established empirically. This correction does not take into account any modification of the pressure in the chamber. At the present time, only a recalibration of the pressure measurement device allows such a modification to be determined.

SUMMARY OF THE INVENTION

One object of the invention is to improve the knowledge of the precision level of the pressure sensor during its use and to avoid having to periodically recalibrate the sensor for preventive purposes. Another object of the invention is to maintain a precision level of the order of 0.1 hPa.

For this purpose, one subject of the invention is a measurement device comprising a resonator and means for measuring a resonant frequency of the resonator, characterized in that it includes means delivering information representative of the quality factor of the resonator at the resonant frequency.

Another subject of the invention is a method of using an air pressure measurement device comprising a pressure sensor and a chamber maintained at a reference pressure, the pressure sensor measuring a pressure difference between the chamber and the air, the sensor comprising a resonator excited by an oscillation controlled by automatic amplitude control means, characterized in that the device includes detection means for detecting a pressure change in the chamber and in that the method consists in comparing a first gain of the unit for automatically controlling the amplitude of the excitation, said gain being measured during the pressure measurement, with a second gain of the unit for automatically controlling the amplitude of the excitation, said gain being calculated at the measured excitation frequency on the basis of parameters defined during a calibration of the device, so as to detect a fault in the device when the difference between the two gains is greater than a given value.

BRIEF DESCRIPTION OF THE DRAWING

The invention will be better understood and other advantages will become apparent on reading the detailed description of one embodiment given by way of example, the description being illustrated by the appended drawing in which.

DETAILED DESCRIPTION OF THE PREFERRED EMBODIMENT

Figure 1:
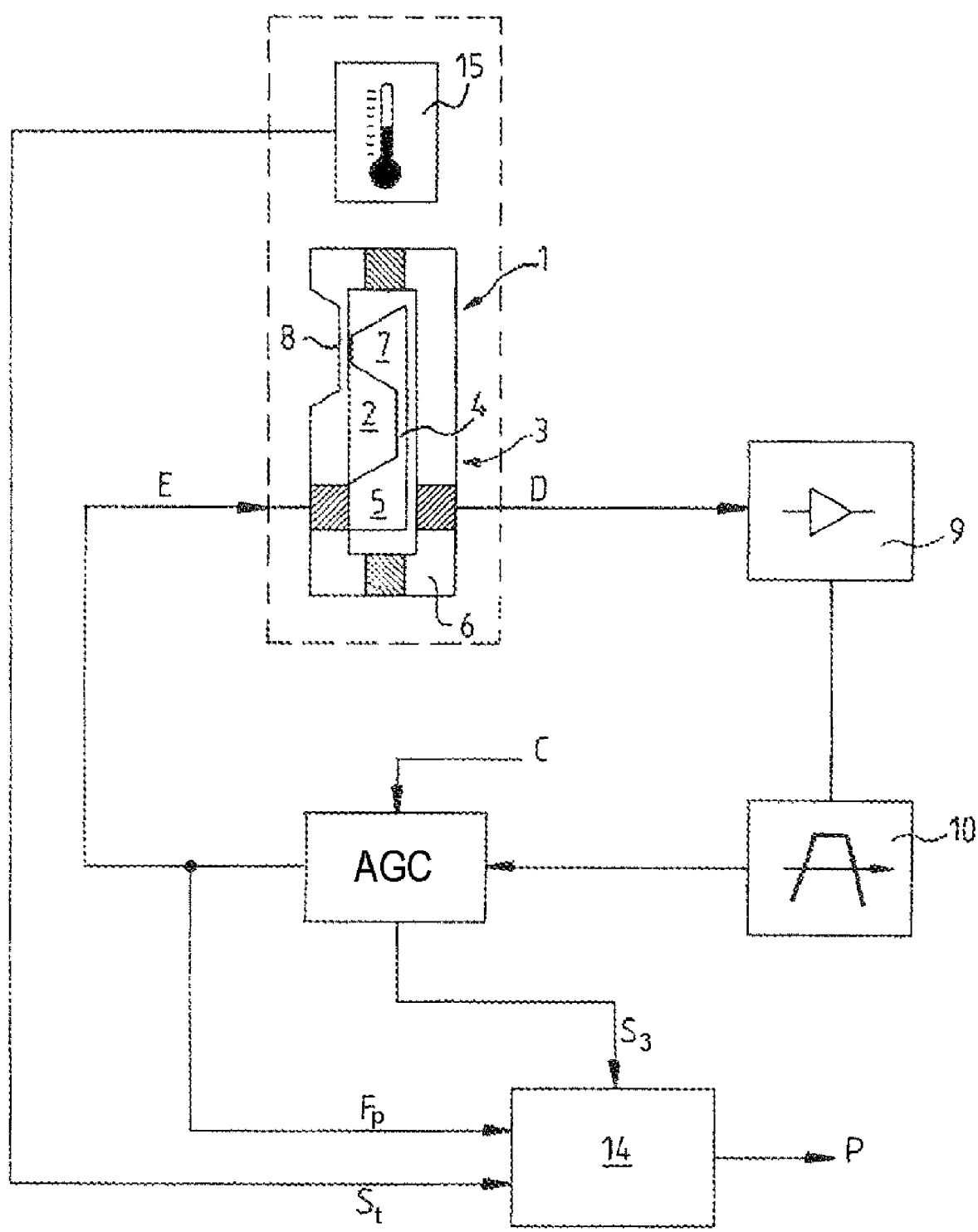
FIG. 1 shows in block diagram form one example of the device according to the invention.

FIG. 1 shows an air pressure measurement device including a pressure sensor 1 and a chamber 2 maintained at a reference pressure, generally close to vacuum. The pressure sensor 1 measures a pressure difference between the chamber 2 and the air surrounding the pressure sensor 1.

Advantageously, the device comprises a resonator 3 and means for measuring a resonant frequency of the resonator 3. The resonator 3 is for example produced by means of a silicon plate 4 which can come into resonance under the effect of an electrical excitation signal E. The silicon plate 4 is located in the chamber 2. The silicon plate 4 is embedded at one of its ends, 5, in a body 6 of the resonator 3 and at the other of its ends, 7, on a thinned wall 8 of the chamber 2. The wall 8 is exposed on one of its faces to the pressure of the air, i.e. the pressure to be measured, and on the other of its faces to the pressure in the chamber 2. The wall 8 deforms according to the pressure difference between the chamber 2 and the air. This deformation of the wall 8 generates a stress in the silicon plate 4. The stress varies with the pressure difference between the air and the chamber 2. The resonant frequency of the silicon plate 4 is therefore also a function of the pressure difference between the air and the chamber 2. A more detailed explanation of the construction of this example of a resonator may be obtained by reading French Patent Application FR 2 687 783. Of course, it is possible to use another type of pressure sensor employing a resonator and in which the resonator is located outside a chamber maintained at a reference pressure.

The resonance is detected by a capacitive effect between the silicon plate 4 and the body 6 of the resonator 3 by means of an electrical signal D taken off from the body 6 of the resonator 3. The electrical signal D is amplified by an amplifier 9 and then filtered by means of a bandpass filter 10, in order to keep only the resonant frequency and to be delivered to means for automatically controlling the amplitude of the excitation signal E, which means are commonly called automatic gain control means, indicated in FIG. 1 as AGC. The automatic gain control unit is controlled by a setpoint C. The automatic gain control unit delivers the excitation signal E, the excitation signal E forming the signal $F_p$ used by a computer 14 to determine the pressure of the air.

The device further includes means 15 for measuring the temperature of the air. The means 15 comprise for example a resistor having a negative temperature coefficient. The means 15 deliver a signal $S_t$ to the computer 14 in order to correct the air pressure measurement. This correction is for example calculated as a function of the signal $S_t$ and of the signal $F_p$ by means of a polynomial function defined during calibration of the device. This calibration is carried out using a campaign of pressure measurements made at different temperatures. The polynomial function is for example of the form:

$$P=A_0+A_1F_p+A_2S_t+A_3F_pS_t+A_4F_p^2S_t+A_5F_pS_t^2\ldots$$

where P represents air pressure and the coefficients $A_i$ represent constants. It has been found that a fifth-order polynomial function provides sufficient precision in the value of the pressure P.

According to the invention, the device includes means for detecting pressure change in the chamber 2. These means advantageously deliver information representative of the quality factor of the resonator at the resonant frequency, for example in the form of a gain $S_3$ of the automatic gain control unit delivered to the computer 14 in order to detect a fault in the device. Moreover, during calibration, the signal $S_3$ was measured for each pressure measurement made. The measurements made during the calibration are used to calculate, for each subsequent pressure measurement, a value that the signal $S_3$ should take if the pressure in the chamber were to remain unchanged. As above, it is found that the signal $S_3$ is a function of the signals $F_p$ and $S_t$ and that this function may be approximated by means of a polynomial function.

To detect a fault in the device, one method consists in comparing a first signal $S_3$, measured during the pressure measurement, with a second signal $S_3$, calculated from parameters defined during calibration of the device and as a function of the measured signals $F_p$ and $S_t$. The device is therefore declared to be faulty if the difference between the measured signal $S_3$ and the calculated signal $S_3$ is greater than a given value. The comparison and the various calculations are made by the computer 14.

Advantageously, it is possible to correct the measurement of the pressure difference between the chamber 2 and the air according to the difference between the two signals $S_3$. For example, the pressure P as a function of the measured signals $F_p$, $S_t$ and $S_3$ is calculated. This calculation may be performed by means of a function, the parameters of which are defined during the calibration phase. Here again, the function is for example a polynomial function. Thus, even if the pressure sensor 1 should drift, owing to a drift of pressure in the chamber 2, it is possible to compensate for this drift using the gain $S_3$ of the automatic gain control unit for controlling the amplitude of the excitation signal E of the resonator 3.

Figure 2:
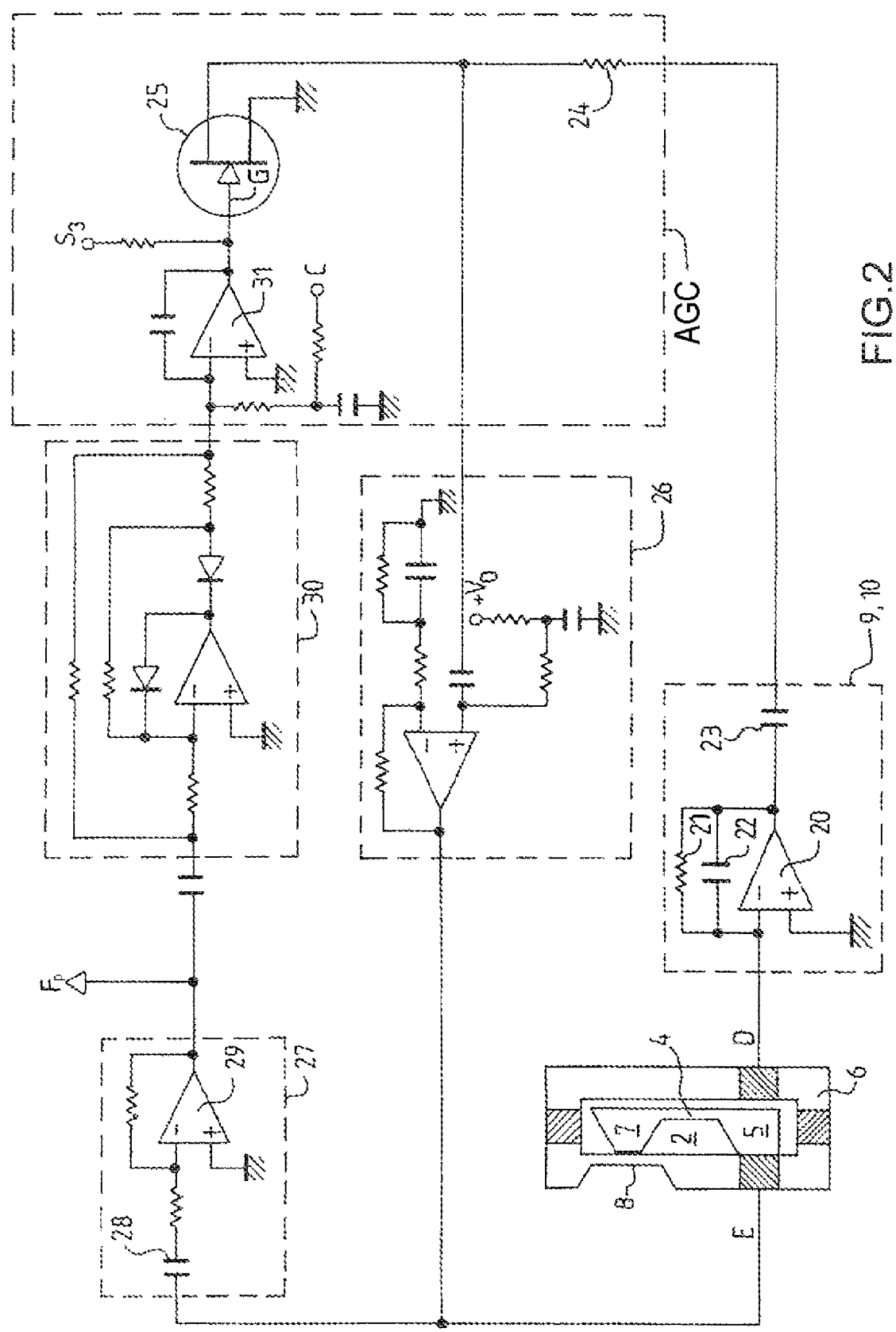
FIG. 2 shows an exemplary embodiment of part of the diagram of FIG. 1.

FIG. 2 shows an exemplary embodiment of a part of the diagram of FIG. 1. In order not to clutter up FIG. 2, the computer 14 and the means 15 for measuring the air temperature have not been shown.

The amplifier 9 and the bandpass filter 10 are formed around an operational amplifier 20 into which the signal D is injected via its inverting input. The non-inverting input of the operational amplifier 20 is connected to ground. A feedback loop of the operational amplifier is formed by a resistor 21 and a capacitor 22 connected in parallel between the inverting input and the output of the operational amplifier 20. A capacitor 23 is connected to the output of the operational amplifier 20 in order to deliver a signal to the automatic gain control unit AGC, which may attenuate this signal by means of a resistor 24 and a field-effect transistor 25. The signal thus attenuated is biased and shaped by passing through a circuit 26. The bias voltage is a voltage $V_0$ delivered to the circuit 26. The output of the circuit 26 delivers the excitation signal E. The signal $F_p$ is formed from the signal E via a circuit 27, the function of which is to debias the signal E by means of a capacitor 28 and to amplify the signal E by means of an operational amplifier 29. The signal $F_p$ is then rectified by means of a circuit 30, before being delivered to the automatic gain control unit AGC. The automatic gain control unit AGC is controlled by a setpoint C. The automatic gain control unit AGC includes an integration first stage produced around an operational amplifier 31, the output of which forms the signal $S_3$ which controls a gate G of the field-effect transistor 25.

It will be readily seen by one of ordinary skill in the art that embodiments according to the present invention fulfill many of the advantages set forth above. After reading the foregoing specification, one of ordinary skill will be able to affect various changes, substitutions of equivalents and various other aspects of the invention as broadly disclosed herein. It is therefore intended that the protection granted hereon be limited only by the definition contained in the appended claims and equivalents thereof.

The invention claimed is:

1. A measurement device comprising:
   a resonator means for measuring a resonant frequency of the resonator;
   means delivering information representative of a quality factor of the resonator at the resonant frequency, the information allowing a fault in the device to be detected; and
   means for comparing a first information representative of a quality factor measured during a pressure measurement and a second information representative of a quality factor measured during a calibration of the device.

2. The device as claimed in claim 1, including a pressure sensor and a chamber maintained at a reference pressure, the pressure sensor measuring a pressure difference between the chamber and the air.

3. The device as claimed in claim 2, including temperature measurement means.

4. The device as claimed in claim 2, including means for correcting the pressure measured by the pressure sensor according to information coming from the means for detecting a pressure change in the chamber.

5. The device as claimed in claim 1, including temperature measurement means.

6. The device as claimed in claim 5, including means for correcting the pressure measured by the pressure sensor according to information coming from the means for detecting a pressure change in the chamber.

7. The device as claimed in claim 1, including means for correcting the pressure measured by the pressure sensor according to a difference between the first information and the second information.

8. The device as claimed in claim 1, including acceleration measurement means.

9. A measurement device comprising:
   a resonator means for measuring a resonant frequency of the resonator;
   means delivering information representative of a quality factor of the resonator at the resonant frequency, the information allowing a fault in the device to be detected; and
   a pressure sensor and a chamber maintained at a reference pressure, the pressure sensor measuring a pressure difference between the chamber and the air, wherein the means for measuring a resonant frequency of the resonator comprises automatic control means for controlling the amplitude of an excitation oscillation of the resonator, and wherein a gain of the automatic amplitude control unit forms the information representative of the quality factor of the resonator.

10. The device as claimed in claim 9, including temperature measurement means.

11. The device as claimed in claim 9, including means for correcting the pressure measured by the pressure sensor according to information coming from the means for detecting a pressure change in the chamber.

12. A method of using an air pressure measurement device comprising the steps of:
   maintaining a pressure sensor
   a chamber at a reference pressure, wherein the pressure sensor measures a pressure difference between the chamber and the air, and
   wherein the pressure sensor comprises:
   a resonator excited by an oscillation controlled by automatic amplitude control means, the principle of the measurement being measuring the resonant frequency, compares a first gain of the amplitude controls means being measured during the pressure measurement, with a second gain of the amplitude control means being calculated at the measured excitation frequency on the basis of parameters defined during a calibration of the device, so as to detect a fault in the device when the difference between the two gains is greater than a given value.

13. The method as claimed in claim 12, wherein the device includes temperature measurement means and wherein the method calculates the second gain as a function of the frequency of the excitation and of the temperature measured during the excitation.

14. The method as claimed in claim 13, comprising correcting the measurement of the pressure difference between the chamber and the air according to the difference between the two gains.

15. The method as claimed claim 12, comprising correcting the measurement of the pressure difference between the chamber and the air according to the difference between the two gains.

16. A method of using an air pressure measurement device comprising the steps of:
   maintaining a pressure sensor and a chamber at a reference pressure;
   measuring a pressure difference between the chamber and air;
   exciting a resonator by oscillation;
   measuring a pressure change in the chamber by detecting a pressure change in the chamber by comparing a first gain of the amplitude control means being measured during said measuring step with a second gain of the amplitude control means being calculated at the measured excitation frequency on the basis of parameters defined during a calibration of the device, so as to detect a fault in the device when the difference between the two gains is greater than a given value.

* * * * *